United States Patent [19]

Dyer, Sr.

[11] Patent Number: 5,352,454

[45] Date of Patent: Oct. 4, 1994

[54] ANTI-CHEWING AND ANTI-CRIBBING COMPOSITION

[75] Inventor: John W. Dyer, Sr., Bartlett, Ill.

[73] Assignee: Dyco Associates, Inc., West Chicago, Ill.

[21] Appl. No.: 925,504

[22] Filed: Aug. 5, 1992

Related U.S. Application Data

[63] Continuation-in-part of Ser. No. 712,399, Jun. 10, 1991, abandoned.

[51] Int. Cl.⁵ ............................................. A01N 25/08
[52] U.S. Cl. .................................... 424/410; 424/405; 514/920; 428/907; 523/122
[58] Field of Search ..................... 424/405, 410–413; 514/918–920, 644–666; 428/907; 524/62, 774, 784

[56] References Cited

U.S. PATENT DOCUMENTS

| | | | |
|---|---|---|---|
| 391 | 9/1837 | Knowles | 427/441 |
| 81,711 | 9/1868 | Van Wagenen | 424/196.1 |
| 707,224 | 6/1901 | Giussani | 427/419.1 |
| 1,469,466 | 12/1922 | Vermeire | 427/441 |
| 2,216,775 | 3/1934 | Helson | 427/298 |
| 2,383,504 | 8/1945 | Luckhaupt | 427/315 |
| 3,269,902 | 8/1966 | Goodhue | 167/46 |
| 3,489,838 | 1/1970 | Goodhue et al. | 424/263 |
| 3,740,201 | 6/1973 | Woodruff | 260/29.7 |
| 3,953,628 | 4/1976 | Gannon | 427/442 |
| 4,965,070 | 10/1990 | Messina | 424/581 |

OTHER PUBLICATIONS

Arena—Poisoning—3rd Edition, pp. 174–175, 1975.
Chem. Abstracts: Pesticides and Controls: Chemical Repellents for the Control of Mammal Damage to Plants, Besser et al., Trans. N. Am. Wildlife Conf., 24, 166–173, (1959), pp. 17136—vol. 57—1962.

Primary Examiner—Thurman K. Page
Assistant Examiner—Neil Levy
Attorney, Agent, or Firm—Charles F. Meroni, Jr.

[57] ABSTRACT

A coating composition to prevent cribbing by a horse includes a solvent, a carrier, a non volatile chemical and a pigment. The solvent comprises a combination of a higher aromatic solvent having a boiling point above 170° Centigrade (380° Fahrenheit), and crystals thereof combined with a carrier therefor. Further, non-volatile chemicals which would assist in penetration of a wood surface and in enhancing residual properties of the composition can be added to the base combination.

17 Claims, No Drawings 5,352,454

ANTI-CHEWING AND ANTI-CRIBBING COMPOSITION

CROSS REFERENCE TO RELATED APPLICATION

This application is a continuation in part of U.S. patent application Ser. No. 07/712,399 now abandoned; filed Jun. 10, 1991, by the same inventive entity.

BACKGROUND OF THE INVENTION

This invention relates to a composition which will minimize, if not altogether eliminate, wood cribbing of animals, such as horses. More particularly, the composition is non-toxic, non-carcinogenic and less flammable than other such available compositions, one embodiment having a proven effectiveness lasting at least six months.

PRIOR ART

Horses, as well as other animals, have at times developed a habit of chewing wood of stalls, fences, paddocks and other structures. A constant chewing of wood by a horse is known in the art as a cribbing habit. This habit is damaging to the structure. Splinters or paint from the wood can also harm the horse. Thus, it is necessary to efficiently prevent the formation of this habit.

In the past, creosote was one chosen chemical for application to the wood to make the same unpalatable to a horse for chewing. In recent years, however, its use has been stopped because it has been found to be toxic and carcinogenic.

To replace creosote with non-toxic or relatively non-toxic organic materials as a coating to stop cribbing and chewing by horses is a highly desired objective. Creosote has an unattractive appearance and is both toxic and carcinogenic. To achieve this result without these dangers, is extremely important. Furthermore, it is useful to provide a decorative and protective finish for the wood in stalls or fences or other confining devices for horses.

These problems have caused the replacement of creosote with other compounds. Presently, relatively harmless but flammable substitutes have been developed. These substitutes include low boiling point aromatic solvents. The lower boiling aromatic solvents such as xylol and toluol are unsatisfactory for two reasons. They are flammable and they evaporate too quickly. The substitutes are also defective in that the effects of such are not long term, lasting only a month or so.

For example, two unpalatable coatings are described in the Messina U.S. Pat. No. 4,965,070, which relates to keeping deer away from gardens and the like, and the Goodhue, et al. U.S. Pat. No. 3,269,902, which relates to keeping cows from chewing through items, such as electrical cables and the like.

Horses in general have a very sensitive mouth and nasal membranes. If a solvent or aromatic solvent which is safe and otherwise harmless, produces a vapor and odor that can irritate those sensitive membranes, the chewing can be stopped. It is very critical to stop horses from chewing on stalls, fences, gates or other wood matters. The requirement for the product is that it be non-toxic, non-flammable, and non-carcinogenic under normal use.

As will be described in greater detail hereinafter, the composition of the present invention has an effect which lasts for at least six months, producing a repellant odor rather than an obnoxious taste, is much less flammable, one embodiment having a flash point above 95° C. (200° F.), and is non-toxic and non-carcinogenic under normal use.

SUMMARY OF THE INVENTION

According to the invention there is provided an anti-cribbing and anti-chewing composition which is to be applied to wood structures and which produces a repellant odor to keep animals, such as horses, from chewing on the wood and ultimately developing a cribbing habit. The composition comprises a resin and/or drying or semi-drying oil dissolved in an aromatic solvent.

Further according to the invention there is provided a method for applying the coating comprising the steps of: gathering ingredients for the coating, including an aromatic solvent having a boiling point above 160° C., crystals of the aromatic solvent, and at least one element selected from the group consisting of a carrier, a pigment, and a non-volatile component; blending the aromatic solvent having a boiling point above 160° C. and crystals of the aromatic solvent to form a homogeneous mixture; adding a carrier to the homogeneous mixture in an amount sufficient to form a coating; and applying the coating to a wood surface in a quantity sufficient to deter chewing of the wood surface.

DESCRIPTION OF THE PREFERRED EMBODIMENTS

The composition of the preferred embodiment of this invention includes a solvent, a carrier, a non volatile chemical and a pigment. The solvent comprises a combination of a higher aromatic solvent having a boiling point above 160° C. (365° Fahrenheit), and crystals thereof with a carrier therefor. Further, non-volatile chemicals which would assist in penetration of a wood surface and in enhancing residual properties of the composition can be added to the base combination.

The key ingredient is the aromatic solvent of exactly the right boiling temperature and vapor pressure. Certainly the high boiling aromatics are used in many areas. However, nobody has discovered the extreme effectiveness of these compositions as a horse repellant material to stop chewing until this invention. This is a new and novel use for these materials.

The key aromatic solvent includes a liquid having a mixture of compounds. Usually the compounds are aromatic and have seven to sixteen carbon atoms. The molecular weight of the solvent is usually 120° to 180°. More preferably, the molecular weight of the solvent is usually 140° to 170°. Most preferably, the molecular weight of the solvent is usually 150° to 166°.

The key ingredient is the aromatic solvent of exactly the right boiling temperature and vapor pressure. Certainly the high boiling aromatics are used in many areas. However, no body has discovered the extreme effectiveness of these compositions as a horse repellant material to stop chewing until this invention. This is a new and novel use for these materials.

The boiling range of the solvent is usually above 160° C. More preferably, the boiling range of the solvent is usually above 170° C. Most preferably, the boiling range of the solvent is usually above 180° C.

The vapor pressure of the solvent at 38° C. is usually 1.2 millimeters of mercury to 12 millimeters of mercury. More preferably, the vapor pressure of the solvent is usually about 1.4 millimeters of mercury up to 10.00 millimeters of mercury. Most preferably, the vapor pressure of the solvent is usually 1.6 millimeters of mercury up to 8 millimeters of mercury.

Most suitably, the main aromatic solvent is that sold under the trade name Aromatic 200 from Exxon, Inc. of New Jersey. This solvent consists predominantly of C9–C15 aromatic hydrocarbons and primarily C10–C12. It has just the right evaporation rate, odor, and condensate properties. All the other materials, resins, asphalt, soy bean oil, pigments, binders, and other components are important only as carriers and colorants.

The second very suitable aromatic solvent is Aromatic 100, also available from Exxon, Inc. consisting predominantly of C8–C10 aromatic hydrocarbons and primarily C9. Aromatic 200 and Aromatic 100 have Chemical Abstracts #64742-94-5-06-9, and #64742-95-6, respectively.

Aromatic 200 and Aromatic 100 as sold by Exxon, Inc., have certain physical characteristic. Typically, the boiling range of these aromatic compounds is in the range of 150° to 293° centigrade. The flash point is in the range of 50° to 105° centigrade. The specific gravity is in the range of 0.872 to 1.00. The vapor pressure at 68° ranges from less than 1 to about 4 millimeters of mercury. The molecular weight range is between 120 and 200. The chemical structure is mostly a single benzene ring with varied lengths of side alkyl chains. The boiling point of the solvent is preferably above 160° centigrade.

There is no coating on the market formulated along these lines for this use as an anticribbing composition. The instant coating was found only through heavy experimentation with a large variety of safe chemicals. There is nothing in technical literature or patents to suggest this coating. The coatings, containing the Aromatic 100 or 200 or mixtures thereof with other elements are effective for 6 months to 1 year.

This coating effectivity has been accomplished by the use of aromatic solvents and crystals, particularly those in the naphthalene class. Aromatic 100 and Aromatic 200 compounds available from Exxon Corporation are typical of the compounds which possess the exact evaporation rate and odor combined with being relatively nonflammable, non-toxic and non-carcinogenic.

The provision of the above non-volatile additives is propounded for assisting in maintained residual properties of the composition. Typical of the non-volatile chemicals which are used are asphalt, hydrocarbon resins and mixtures thereof. Typical examples thereof are Tellura 797 (available from EXXON) and Petrorez 140 available from Lawter International, Inc. of Northbrook, Ill. Other compatible resins such an maleic and phenolic may also be used. Aliphatic middle distillate petroleum hydrocarbons are also well known. An especially suitable one is sold under the mark Magiesol #52 by Magie Brothers Oil Company of Franklin Park, Ill. The efficiency of the coating may further be improved by adding to the coating more crystals of the solvent.

Suitable carriers which are used include alkali refined soy bean oil. Typical examples thereof are refined by Cargill, Inc. of Carpentersville, Ill., and Reichold Chemicals, Inc. of Morris, Ill. Other suitable carriers include oils such as linseed oil.

By addition of a pigment, the coat becomes attractive as well as effective. Typical pigments include, for a black coating, carbon black. Titanium dioxide can produce a white coating. This pigment requirement varies by the degree of opacity and whiteness desired. Further colors of the composition could be produced as desired as well, by using the formula in Table B and adding a particular pigment thereto, such as Ouinacridone Red, Phthalocyanine Blue, and others.

The aromatic solvent is present in the composition at the range of 20 to 70 percent by weight, non-volatile additives 5 to 40 percent by weight, carrier 5 to 40 percent by weight, and pigment 5 to 40 percent by weight. More preferably, the aromatic solvent is present in the composition at the range of 25 to 65 percent by weight, non-volatile additives 10 to 35 percent by weight, carrier 10 to 35 percent by weight, and pigment 10 to 35 percent by weight. Most preferably, the aromatic solvent is present in the composition at the range of 30 to 60 percent by weight, non-volatile additives 15 to 30 percent by weight, carrier 15 to 30 percent by weight, and pigment 15 to 30 percent by weight.

By using the defined aromatic solvent and crystals, cribbing can be stopped. It is critical that the solvent used fall within boiling point range, vapor pressure range and flashpoint range as described. This stain or other coating containing this composition may be applied to wood to prevent a horse from engaging in cribbing. A coating of this invention may be applied in any suitable fashion to a wood or other suitable surface. Typical application instruments include, but are not limited to, a brush, a roller, a spraying device or a dip tank.

In the following examples, which are intended to illustrate without unduly limiting the invention, all parts and percentages are by weight unless otherwise specified.

EXAMPLE 1

The ingredients of Table A are assembled.

TABLE A

| MATERIAL | PERCENT | CAS# |
| --- | --- | --- |
| Asphalt | 40.00 | 8052-42-4 |
| High B.P. Hydrotreatec Petroleum Distillate | 10.00 | 64742-54-7 |
| Heavy Aromatic Solvent | 33.00 | 64742-94-5 & 06-9 |
| Aliphatic Middle Distillate | 17.00 | 64742-46-7 |
| | 100.00 | |

The asphalt, high boiling point petroleum distillate and heavy aromatic solvent having the indicated Chemical Abstracts Number (CAS#) are blended sufficiently to form a homogeneous mixture. The aliphatic middle distillate is added to the homogeneous mixture and blended to obtain a proper coating viscosity. The resultant composition, which resembles a dark oak stain, is then applied to a section of a corral. Two horses known to have a cribbing habit are placed in the corral and observed. Each horse continued to chew on the corral, except when they approached the treated section. When each horse approached the treated section, the upper lip curled and the nostrils flared indicating an objection to the odor and a refusal to chew on the treated section. The treated section remains unchewed for eight months.

EXAMPLE 2

The procedure of Example 1 is repeated except that the coating is formed from 61.34% by weight of the coating of Example 1, 20% Aromatic 200 and a balance of 18.76 carbon black concentrate to form a black coating.

For the carbon black concentrate, 30–40% carbon black is mixed in a vehicle similar to the mixture of Example 1. This composition is then pumped to shot mills, ground to a very fine dispersion and stored as a concentrate. The concentrate is added as above indicated.

The resultant composition is then applied to a section of a corral. Two horses known to have a cribbing habit are placed in the corral and observed. Each horse continued to chew on the corral, except when they approached the treated section. When each horse approached the treated section, the upper lip curled and the nostrils flared indicating an objection to the odor and a refusal to chew on the treated section. The treated section remains unchewed for six months.

EXAMPLE 3

The procedure of Example 2 is repeated except that the carbon black concentrate is replaced with titanium dioxide and the vehicle is identical to Example 4 (a clear or colorless coating). The color is white, decorative and effective.

The titanium dioxide pigment is obtained by a procedure wherein 40–50% titanium dioxide is mixed and milled in the clear or colorless coating and then adjusted in for strength and viscosity by further let down with the colorless or clear coating to approximately 10–15% pigment. This pigment requirement varies on the degree of opacity and whiteness desired.

EXAMPLE 4

The procedure of Example 1 is repeated with the composition being defined as in Table B.

TABLE B

| MATERIAL | PERCENT | CAS# |
| --- | --- | --- |
| Lt. Aromatic C-9 Hydrocarbon Resin | 20.00 | 68131-99-7 |
| Alkali Refined Soy Bean Oil | 20.00 | 8001-22-7 |
| Heavy Aromatic Solvent and a Middle Distillate Solvent | 60.00 | See below |
|  | 100.00 |  |

The heavy aromatic solvent has a Chemical Abstracts Number of 64742-94-5. The middle distillate solvent has a Chemical Abstracts Number of 64742-06-9.

The hydrocarbon resin is cooked into the alkali refined soy bean oil at about 150° C. (300° F.) for a time sufficient to form a solution. The aromatic solvent is then added. A sufficient amount of middle distillate solvent is added to adjust viscosity. The resultant composition is substantially clear or virtually colorless.

Upon cooling to air temperature, this composition is then applied to a section of a stall. A horse known to have a cribbing habit is placed in the stall and observed. The horse continued to chew on the stall, except when he approached the treated section. When the horse approached the treated section, the upper lip curled and the nostrils flared indicating an objection to the odor and a refusal to chew on the treated section.

This application—taken as a whole with the specification, claims and abstract provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modifications of this composition can become clear to a person having ordinary skill in this particular art. Such modifications are clearly covered by this disclosure.

What is claimed and sought to be protected by Letters Patent of the United States is:

1. A method for preventing chewing of wood by applying coating, having an odor objectionable to a horse, to a wood surface, wherein said method comprises the steps of:
    (a) gathering ingredients for said coating consisting of (1) an aromatic solvent of 120–200 molecular weight having a boiling point range of 160°–293° C., a flash point range of 50°–105° C., a vapor pressure of below 1–4 millimeters of mercury at 8° C., crystals of said aromatic solvent, (2) a liquid carrier from the group consisting of an alkali refined soy bean oil and linseed oil, (3) a pigment, and (4) a non-volatile component carrier and binder from the group consisting of hydrocarbon resin, maleic resin and phenolic resin;
    (b) blending said aromatic solvent and crystals if the crystals are not firmly within the aromatic solvent to form a homogeneous mixture;
    (c) adding carrier, pigment and non-volatile component carrier and binder to said homogeneous mixture to form a coating wherein the aromatic is 20–70% carrier 5–40% and the non-volatile component carrier and binder 5–40% of the coating by weight; and
    (d) applying the coating to a wood surface in a quantity sufficient to deter the horse from chewing said wood surface.
2. The method of claim 1, wherein said aromatic solvent is Aromatic 200.
3. The method of claim 1, wherein said aromatic solvent is Aromatic 100.
4. The method of claim 1, wherein said aromatic solvent includes aromatic hydrocarbons having from 8 to 16 carbon atoms and said aromatic solvent contains primarily aromatic hydrocarbons having from 10 to 12 carbon atoms.
5. The method of claim 4, wherein:
    (a) said pigment is selected from the group consisting of carbon black, titanium dioxide, Quinacridone Red and Phthalocyanine Blue;
    (b) said aromatic solvent being present at the range of 30 to 60 percent by weight, said non-volatile component carrier and binder being present at the range of 15 to 30 percent by weight, said carrier being present at the range of 15 to 30 percent by weight, and said pigment being present at the range of 15 to 30 percent by weight; and
    (c) the step of applying the coating is accomplished by at least one device selected from a group consisting of a brush device, a roller device, a spraying device, or a dip tank device.
6. A horse repellant coating composition which has an odor objectionable to a horse and prevents the chewing of wood by the horse, consisting of:
    (a) 20–70% by weight of an aromatic solvent of 120–200 molecular weight having a boiling point range of 160°–293° C., a flash point range of 50°–105° C., a vapor pressure of below 1–4 millimeters of mercury at 38° C. and crystals of said aromatic solvent;

(b) 5–40% by weight of a liquid carrier selected from the group consisting of an alkali refined soy bean oil and linseed oil;

(c) 5–40% by weight of a pigment; and (d) 5–40% by weight of a non-volatile component carrier and binder from the group consisting of hydrocarbon resin, maleic resin and phenolic resin.

7. The coating composition of claim 6, wherein said aromatic solvent is present at the range of 25–65% by weight, said non-volatile component carrier and binder is present at the range of 10–35%, said liquid carrier is present at the range of 10–35% by weight, and said pigment is present at the range of 10–35% by weight.

8. The coating composition of claim 6, wherein said aromatic solvent is present at the range of 30–60% by weight, said non-volatile component carrier and binder is present at the range of 15–30% by weight, said liquid carrier is present at the range of 15–30% by weight, and said pigment is present at the range of 15–30% by weight.

9. The coating composition of claim 6, wherein said aromatic solvent includes aromatic hydrocarbons having from 8 to 16 carbon atoms and said aromatic solvent contains primarily aromatic hydrocarbons having from 10 to 12 carbon atoms.

10. The coating composition of claim 6, wherein said pigment is selected from the group consisting of carbon black, titanium dioxide, Quinacridone Red and Phthalocyanine Blue.

11. The coating composition of claim 6, wherein:
a. said aromatic solvent has a molecular weight of about 140 to about 170; and
b. said aromatic solvent has a vapor pressure of about 1.4 millimeters to about 10 millimeters of mercury.

12. The coating composition of claim 11, wherein:
a. said aromatic solvent has molecular weight of about 150 to about 166;
b. said aromatic solvent has a boiling range above about 180° Centrigrade; and
c. said aromatic solvent has a vapor pressure of about 1.6 millimeters to about 8 millimeters of mercury.

13. The coating composition of claim 12, wherein:
a. said aromatic solvent includes aromatic hydrocarbons having from 9 to 16 carbon atoms; and
b. said aromatic solvent contains primarily aromatic hydrocarbons having from 10 to 12 carbon atoms.

14. The coating composition of claim 6, wherein said composition is applied to a wood surface by at least one device selected from the group consisting of a brush device, a roller device, a spraying device, or a dip tank device.

15. The coating composition of claim 6, wherein said aromatic solvent includes a t least one liquid having 10 to 12 carbon atoms.

16. The coating composition of claim 6, wherein:
a. said aromatic solvent has a molecular weight of about 140 to about 170;
b. said aromatic solvent has a boiling range above about 170° Centigrade; and
c. said aromatic solvent has a vapor pressure of about 1.4 millimeters to about 10 millimeters of mercury.

17. The coating composition of claim 16, wherein:
a. said aromatic solvent has a molecular weight of about 150 to about 166;
b. said aromatic solvent has a boiling range above about 180° Centrigrade; and
c. said aromatic solvent has a vapor pressure of about 1.6 millimeters to about 8 millimeters of mercury.

* * * * *

UNITED STATES PATENT AND TRADEMARK OFFICE
CERTIFICATE OF CORRECTION

PATENT NO. : 5,352,454
DATED : Oct. 4, 1994
INVENTOR(S) : John W. Dyer, Sr.

It is certified that error appears in the above-indentified patent and that said Letters Patent is hereby corrected as shown below:

In col. 2, line 51, replace "120°" with --120--

In col. 2, line 51, replace "180°" with --180--

In col. 2, line 53, replace "140°" with --140--

In col. 2, line 53, replace "170°" with --170--

In col. 2, line 54, replace "150°" with --150--

In col. 2, line 54, replace "166°" with --166--

In col. 6, line 18, replace "8°" with --38°--

Signed and Sealed this

Thirteenth Day of June, 1995

Attest:

BRUCE LEHMAN

Attesting Officer

Commissioner of Patents and Trademarks